United States Patent [19]

De Baetselier et al.

[11] Patent Number: 5,585,257
[45] Date of Patent: Dec. 17, 1996

[54] PROCESS FOR THE PRODUCTION OF HUMAN LYSOZYME

[75] Inventors: Annie De Baetselier, Berchem, Belgium; Steven Rosenberg, Oakland, Calif.; Jacques D. V. Hanotier, Lasne, Belgium

[73] Assignees: Fina Research S.A., Feluy, Belgium; Chiron Corporation, Emeryville, Calif.

[21] Appl. No.: 684,470

[22] Filed: Apr. 11, 1991

Related U.S. Application Data

[63] Continuation of Ser. No. 249,413, Sep. 26, 1988, abandoned.

[51] Int. Cl.$^6$ .............................. C12N 9/36; C12N 5/00
[52] U.S. Cl. ................ 435/206; 435/69.1; 435/69.7; 435/69.8; 435/172.1; 435/172.3; 435/254.1; 435/254.11; 435/254.2; 435/254.21; 435/255.1; 435/255.2; 435/255.21; 435/320.1; 536/23.1; 536/23.4; 536/23.5
[58] Field of Search .......................... 435/172.3, 172.1, 435/206, 255, 69.1, 69.7, 69.8, 172.1, 172.3, 252.3, 254.1, 254.11, 254.2, 254.21, 255.1, 255.2, 255.21, 320.1, 206; 935/37, 69; 536/23.1, 23.4, 23.5

[56] References Cited

U.S. PATENT DOCUMENTS

| | | | |
|---|---|---|---|
| 4,595,658 | 6/1986 | Zinder et al. | 435/69.1 |
| 4,624,922 | 11/1986 | Horikoshi et al. | 435/91.41 |
| 4,767,708 | 8/1988 | Minkley et al. | 435/194 |
| 4,880,734 | 5/1989 | Burke et al. | 435/69.1 |
| 5,124,256 | 6/1992 | Crahay et al. | 435/71.1 |

FOREIGN PATENT DOCUMENTS

| | | |
|---|---|---|
| 903626 | 3/1986 | Belgium . |
| 0164556 | 12/1985 | European Pat. Off. . |
| 0213593 | 3/1987 | European Pat. Off. . |

OTHER PUBLICATIONS

Yeast Promoters: Positive and Negative Elements, *Minireviews*, Cell, vol. 36, 799–800, Apr. 1984.

The Yeast PH05 promoter: Phosphate–control elements and sequences mediating mRNA start–site selection, *Prac. Natl. Acad. Sci, USA*, vol. 84, pp. 1340–1344, Mar. 1987.

Vectors for Cloning in Yeast, Curr. Top. Microbiol. Immunol. 96, Albert Hinnen and Bernd Meyhack, 101–117 (1982).

Kumagai et al. (1987), J. Biochem., vol. 102, pp. 733–740.

Taniyama et al. (1988), Biochem. Biophys. Res. Com., vol. 152, pp. 962–967.

Artymiuk et al. (1981), J. Mol. Biol., vol. 152, pp. 737–762.

Jigami et al. (1986), "Expression of human–lysozyme in *S. cerevisiae*," Gene, vol. 43, pp. 273–279.

Yoshimura et al. (1987), "Differences between *S. cerevisiae* and *B. subtilis* in secretion of human lysozyme," BBRC, vol. 145, pp. 712–718.

Cousens et al. (1987), "High level of expression in yeast," Gene, vol. 61, pp. 265–275.

*Primary Examiner*—David Guzo
*Attorney, Agent, or Firm*—Roger W. Parkhurst; M. Norwood Cheairs

[57] ABSTRACT

Yeast cells whose DNA has been appropriately engineered to produce and to secrete lysozyme under control of a regulatable promoter are grown in the substantial absence of lysozyme synthesis and then are induced to produce and to secrete lysozyme under growth-limited conditions. This process is particularly suitable for the production of human lysozyme or mutants thereof.

43 Claims, 10 Drawing Sheets

FIG. 1

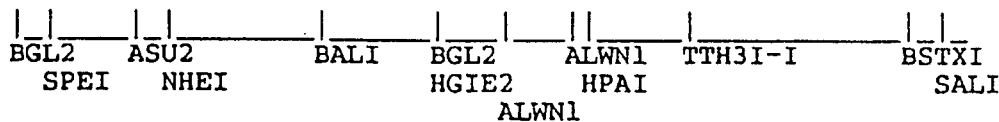

```
        MetArgSerLeuLeuIleLeuValLeuCysPheLeuProLeuAlaAlaLeuGlyLysVal
  1  CATGAGATCTTTGTTGATACTAGTTTTGTGTTTCTTGCCATTGGCTGCTTTGGGTAAGGTT
        TCTAGAAACAACTATGATCAAAACACAAAGAACGGTAACCGACGAAACCCATTCCAA
```

4 BGL2, 18 SPEI,

```
        PheGluArgCysGluLeuAlaArgThrLeuLysArgLeuGlyMetAspGlyTyrArgGly
 61  TTCGAAAGATGTGAGCTAGCTAGAACTTTGAAGAGATTGGGTATGGACGGTTACAGAGGT
        AAGCTTTCTACACTCGATCGATCTTGAAACTTCTCTAACCCATACCTGCCAATGTCTCCA
```

61 ASU2, 75 NHEI,

```
        IleSerLeuAlaAsnTrpMetCysLeuAlaLysTrpGluSerGlyTyrAsnThrArgAla
121  ATCTCCTTGGCTAACTGGATGTGTTTGGCCAAGTGGGAATCTGGTTACAACACCAGAGCT
        TAGAGGAACCGATTGACCTACACAAACCGGTTCACCCTTAGACCAATGTTGTGGTCTCGA
```

146 BALI,

```
        ThrAsnTyrAsnAlaGlyAspArgSerThrAspTyrGlyIlePheGlnIleAsnSerArg
181  ACCAACTACAACGCTGGTGACAGATCTACCGACTACGGTATCTTCCAAATCAACTCCAGA
        TGGTTGATGTTGCGACCACTGTCTAGATGGCTGATGCCATAGAAGGTTTAGTTGAGGTCT
```

202 BGL2, 208 HGIE2, 237 ALWN1,

```
        TyrTrpCysAsnAspGlyLysThrProGlyAlaValAsnAlaCysHisLeuSerCysSer
241  TACTGGTGTAACGACGGTAAGACCCCAGGTGCTGTTAACGCTTGTCACTTGTCCTGTTCT
        ATGACCACATTGCTGCCATTCTGGGGTCCACGACAATTGCGAACAGTGAACAGGACAAGA
```

266 ALWN1, 274 HPAI,

```
        AlaLeuLeuGlnAspAsnIleAlaAspAlaValAlaCysAlaLysArgValValArgAsp
301  GCTTTGTTGCAAGACAACATCGCTGACGCTGTCGCCTGTGCTAAGAGAGTTGTTAGAGAC
        CGAAACAACGTTCTGTTGTAGCGACTGCGACAGCGGACACGATTCTCTCAACAATCTCTG
```

325 TTH3I,

```
        ProGlnGlyIleArgAlaTrpValAlaTrpArgAsnArgCysGlnAsnArgAspValArg
361  CCACAAGGTATCAGAGCTTGGGTTGCTTGGAGAAACAGATGTCAAAACAGAGACGTTAGA
        GGTGTTCCATAGTCTCGAACCCAACGAACCTCTTTGTCTACAGTTTTGTCTCTGCAATCT
```

```
        GlnTyrValGlnGlyCysGlyValOC
421  CAATACGTCCAAGGTTGTGGTGTTTAAG
        GTTATGCAGGTTCCAACACCACAAATTCAGCT
```

429 BSTXI, 448 SALI,

FIG. 3

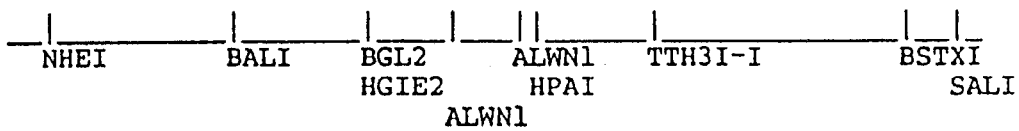

```
                                                GLY
      LysValPhe    ArgCysGluLeuAlaArgThrLeuLysArgLeuGlyMetAspGlyTyr
   1  AAGGTTTTCGGAAGATGTGAGCTAGCTAGAACTTTGAAGAGATTGGGTATGGACGGTTAC
      TTCCAAAAGCCTTCTACACTCGATCGATCTTGAAACTTCTCTAACCCATACCTGCCAATG

21  NHEI,

ArgGlyIleSerLeuAlaAsnTrpMetCysLeuAlaLysTrpGluSerGlyTyrAsnThr
  61  AGAGGTATCTCCTTGGCTAACTGGATGTGTTTGGCCAAGTGGGAATCTGGTTACAACACC
      TCTCCATAGAGGAACCGATTGACCTACACAAACCGGTTCACCCTTAGACCAATGTTGTGG

92  BALI,

ArgAlaThrAsnTyrAsnAlaGlyAspArgSerThrAspTyrGlyIlePheGlnIleAsn
 121  AGAGCTACCAACTACAACGCTGGTGACAGATCTACCGACTACGGTATCTTCCAAATCAAC
      TCTCGATGGTTGATGTTGCGACCACTGTCTAGATGGCTGATGCCATAGAAGGTTTAGTTG

148  BGL2, 154 HGIE2,

SerArgTyrTrpCysAsnAspGlyLysThrProGlyAlaValAsnAlaCysHisLeuSer
 181  TCCAGATACTGGTGTAACGACGGTAAGACCCCAGGTGCTGTTAACGCTTGTCACTTGTCC
      AGGTCTATGACCACATTGCTGCCATTCTGGGGTCCACGACAATTGCGAACAGTGAACAGG

183  ALWN1, 212 ALWN1, 220 HPAI,

CysSerAlaLeuLeuGlnAspAsnIleAlaAspAlaValAlaCysAlaLysArgValVal
 241  TGTTCTGCTTTGTTGCAAGACAACATCGCTGACGCTGTCGCCTGTGCTAAGAGAGTTGTT
      ACAAGACGAAACAACGTTCTGTTGTAGCGACTGCGACAGCGGACACGATTCTCTCAACAA

271  TTH3I,

ArgAspProGlnGlyIleArgAlaTrpValAlaTrpArgAsnArgCysGlnAsnArgAsp
 301  AGAGACCCACAAGGTATCAGAGCTTGGGTTGCTTGGAGAAACAGATGTCAAAACAGAGAC
      TCTCTGGGTGTTCCATAGTCTCGAACCCAACGAACCTCTTTGTCTACAGTTTTGTCTCTG

ValArgGlnTyrValGlnGlyCysGlyValOC ValAsp
 361  GTTAGACAATACGTCCAAGGTTGTGGTGTTTAAGTCGAC
      CAATCTGTTATGCAGGTTCCAACACCACAAATTCAGCTG

375  BSTXI, 394 SALI,
```

PROCESS FOR THE PRODUCTION OF HUMAN LYSOZYME

This is a Continuation of application Ser. No. 07/249,413 filed Sep. 26, 1988, now abandoned.

DESCRIPTION OF THE TECHNICAL FIELD

The present invention relates to a process for the production of active human lysozyme by cultivation of yeasts genetically manipulated for this purpose. More particularly, it relates to a process wherein active human lysozyme is produced in high yield and secreted by the yeast cells from which it can easily be recovered and purified.

Lysozyme is the common name given to enzymes widely spread in nature and known to catalyze the hydrolysis of peptidoglycan which is the major component of the bacterial cell wall. As a result of this activity, lysozymes have an antibacterial action and, for this reason, are believed to participate in the various barriers to bacterial infection possessed by most living organisms. Thus, in insects which lack lymphocytes and immunoglobulins, the immune response to bacterial infection is ensured by a multifactorial enzyme system of which lysozyme is an important component (see for example D. HULTMARK et al., Eur. J. Biochem. 106, 7, 1980). In higher animals, although the physiological role of lysozyme is still not known (see R. RAGHUNATHAN, IRCS Med. Sci. 13, 480, 1985), its ubiquitous distribution suggests this role might be important. It has been suggested that it could have a stimulating action on the immune system (see P. JOLLES, Biomedicine 25, 276, 1976). Human lysozyme at physiological doses was shown to stimulate in vitro phagocytosis of yeast cells by polymorphonuclear leucocytes (see M. KLOCKARS & P. ROBERTS, Acta haemat. 58, 289, 1976). It has also been suggested that lysozyme might have a general role of surveillance of membranes and in the anti-tumor functions of macrophages (see E. F. OSSERMAN et al., Nature 243, 331, 1973). More recently, it has been shown that lysozyme itself has some anti-tumor action (see R. RAGHNATHAN, Cancer Detection and Prevention 5, 78, 1982). Already, chicken lysozyme is used, especially in Japan, for a variety of pharmaceutical applications.

Chicken lysozyme belongs to a class of closely related enzymes which also includes human lysozyme and which are referred to as c (chicken) lysozymes. They are characterized by similar physicochemical properties which include: a molecular weight of about 15,000, close homology in amino acid sequence and tertiary structure, the same enzymatic activity, e.g. some chitinase activity, in contrast with g (goose) lysozymes which have a molecular weight of about 20,000 and no chitinase activity (For a review, see P. JOLLES & J. JOLLES, Mol. & Cell. Biochem. 63, 165, 1984).

However, despite these structural and physicochemical similarities, lysozymes within the same class may have quite different immunological properties. For example, chicken lysozyme and human lysozyme do not cross-react with their respective antibodies (see A. FAURE & P. JOLLES, FEBS Lett. 10, 237, 1970). Therefore, human lysozyme is especially indicated for pharmaceutical and even for food uses. However, unlike chicken lysozyme for which an abundant source exists and is actually exploited, i.e. from egg white, human lysozyme cannot be provided in large amounts for commercial purposes except by culturing cells whose DNA has been especially manipulated to express the enzyme.

It is now current practice to clone and express in a microbial host a gene coding for a heterologous protein, e.g. a protein of human origin. Numerous examples can be found with great details in the patent literature, some of which have already reached commercial fruition. This is the case for e.g. human insulin, growth hormone and alpha-interferon expressed in the gram-negative bacterium *Escherichia coli*. In this host, high expression levels can easily be obtained; however, the protein thus produced is frequently concentrated as large inclusion bodies where it is in insoluble and inactive form. In such cases, in order to obtain the physiologically active protein, it is necessary to apply a costly and tedious procedure of renaturation, the yield of which may be as low as about 20% as is the case of prochymosin (see F. A. O. MARSTON et al., Biotechnology 2, 800, 1984). The same type of phenomenon apparently takes place when a DNA segment coding for human lysozyme is expressed in *E. coli*. After sonication of the cells, the synthesized human lysozyme is found mainly associated with the cell debris. Moreover, the protein is not active and differs from the native human lysozyme by the presence of an additional N-terminal methionine residue (see M. MURAKI et al., Agric. Biol. Chem. 49, 2829, 1985).

To obviate these difficulties, attempts were made to express human lysozyme in the gram-positive bacterium *Bacillus subtilis*, which is known to secrete actively a number of hydrolytic enzymes into the external medium and which is extensively used as host for the expression and secretion of heterologous proteins. However, in the case of human lysozyme it was recently shown that the secreted protein is enzymatically inactive, probably through incorrect bond formation (see K. YOSHIMURA et al., Biochem. & Biophys. Res. Comm. 145, 712, 1987).

Hosts other than bacteria can also be used for the production of heterologous protein e.g. eukaryotic microorganisms such as yeasts, especially *Saccharomyces cerevisiae*, or even filamentous fungi. A typical example of the production in high yield of a human protein in yeast is the intracellular expression of active superoxide dismutase (see International patent application WO 85/01503). However, when DNA coding for mature human lysozyme is expressed in yeast, the same phenomenon as observed in *E.coli* takes place, i.e. lysozyme is found associated with cell debris from which it has to be extracted by solubilizing agents such as concentrated urea. (see European patent application EP 0181634, p. 47). More recently, further data were provided which show that mature lysozyme expressed in yeast is indeed obtained in insoluble and inactive form, probably as a result of incorrect formation of disulfide bonds (see T. HAYAKAWA et al., Gene 56, 53, 1987).

As disclosed in Belgian patent BE 901,223, enzymatically active lysozyme can be obtained from genetically manipulated yeasts provided that DNA coding for the mature protein is fused with a leader sequence coding for a signal peptide recognized by the secretion machinery of the yeast cell. In this case, the mature protein is secreted through the plasma membrane and then, to an extent depending on conditions, excreted into the culture medium. In said Belgian patent, it is thus shown that expressing in yeast a complete cDNA coding for chicken prelysozyme results in the production of enzymatically-active lysozyme, a large portion of which, i.e. about 73%, is found solubilized in the culture medium. Later it was shown that the N-terminal sequence of the chicken lysozyme thus produced is identical to that of the native enzyme, i.e. Lys-Val-Phe-Gly-Arg-Cys-Glu-Leu-Ala-Ala (see J. OBERTO et al., 11th Int. Symp. Special. Yeast Mol. Biol. & Genetics, Varna, Nov. 4–9, 1985; also see Belgian patent BE 903,626). These results demonstrate that the signal sequence of chicken lysozyme is correctly cleaved by the yeast secretion system, making it possible to use said signal sequence to ensure secretion of lysozymes from various sources as claimed in Belgian patent BE 901,223, claim 3 for example. Advantage of this was recently taken in the case of human lysozyme (see Y. JIGAMI et al., Gene 43, 273, 1986 and K. YOSHIMURA et al., ref. cit.). However, the yields reported are relatively small.

The possibility to have lysozyme secreted from the yeast cells is of great practical advantage. Not only is the enzyme thus obtained active and identical to the native protein, but it is easily recovered and purified by known methods such as those described in Belgian patent BE 903,626, supra, without having to grind the cells and to apply complex and costly fractionation and renaturation procedures. Still another advantage of having the desired protein secreted from the cells is the possibility of recovering the latter for some secondary use, e.g. as a source of proteins and vitamins in feed formulations. Actually, the high protein content of yeasts, their good amino acid balance and the absence of cellulose therefrom make them a valuable feed supplement for young husbandry animals such as calves and piglets.

BRIEF SUMMARY OF THE INVENTION

For the production by fermentation of a relatively high-volume, medium-value enzyme such as lysozyme to be economically feasible, it is not enough that provision be made to have it secreted from the cells. It is also necessary to produce it in high yield. Accordingly, it is an object of this invention to provide an improved process for the production in high yield of enzymatically-active lysozyme. It is a further object thereof to achieve this production under such conditions that denaturation of the enzyme is minimized and that it is obtained in a concentrated form easily processed for further purification. This invention is of particular interest when the lysozyme produced is relatively toxic for the yeast cell, more particularly when human lysozyme is to be produced. Other objects and advantages of the invention will become apparent from the following description and from the examples.

These objects are accomplished by application of a fermentation process wherein yeast cells whose DNA has been appropriately engineered are induced to produce and to secrete human lysozyme under growth-limited conditions.

In one aspect, the present invention relates to a process for the production of enzymatically active lysozyme comprising:

contacting growing yeast cells whose DNA has been genetically engineered with a culture medium under growth-limited conditions, and inducing said yeast cells to synthesize and secrete enzymatically-active lysozyme.

In another aspect, the present invention relates to a process for the production of enzymatically-active lysozyme comprising:

growing yeast cells whose DNA has been genetically engineered in a culture medium which represses synthesis of enzymatically-active lysozyme, contacting said growing yeast cells into a culture medium under growth-limited conditions, and inducing said yeast cells to synthesize and secrete enzymatically-active lysozyme.

In another aspect, the present invention relates to a synthetic gene for human lysozyme, selected from the group comprising the following sequence

```
AAGGTTTTCGAAAGATGTGAGCTAGCTAGAACTTTGAAGAGATTGGGTATGGACGGTTACAGAGGTATCTCCTTGGCTAACTGGATG
TTCCAAAAGCTTTCTACACTCGATCGATCTTGAAACTTCTCTAACCCATACCTGCCAATGTCTCCATAGAGGAACCGATTGACCTAC

TGTTTGGCCAAGTGGGAATCTGGTTACAACACCAGAGCTACCAACTACAACGCTGGTGACAGATCTACCGACTACGGTATCTTCCA
ACAAACCGGTTCACCCTTAGACCAATGTTGTGGTCTCGATGGTTGATGTTGCGACCACTGTCTAGATGGCTGATGCCATAGAAGGT

AATCAACTCCAGATACTGGTGTAACGACGGTAAGACCCCAGGTGCTGTTAACGCTTGTCACTTGTCCTGTTCTGCTTTGTTGCAAG
TTAGTTGAGGTCTATGACCACATTGCTGCCATTCTGGGGTCCACGACAATTGCGAACAGTGAACAGGACAAGACGAAACAACGTTC

ACAACATCGCTGACGCTGTCGCCTGTGCTAAGAGAGTTGTTAGAGACCCACAAGGTATCAGAGCTTGGGTTGCTTGGAGAAACAGA
TGTTGTAGCGACTGCGACAGCGGACACGATTCTCTCAACAATCTCTGGGTGTTCCATAGTCTCGAACCCAACGAACCTCTTTGTCT

TGTCAAAACAGAGACGTTAGACAATACGTCCAAGGTTGTGGTGTT
ACAGTTTTGTCTCTGCAATCTGTTATGCAGGTTCCAACACCACAA
``` and the mutants thereof coding for a protein which is different from native human lysozyme and which retain a muramidase activity.

BRIEF DESCRIPTION OF THE FIGURES

FIG. 1 illustrates a sequence of a synthetic gene coding for human lysozyme, which was synthesized with yeast preferred codons (J. L. BENNETZEN and B. D. HALL, J. Biol. Chem. 257, 3026, 1982) using phosphoramidite chemistry on an Applied Biosystems DNA Synthesizer.

FIG. 3 illustrates a sequence of a mutant human lysozyme gene with Gly-4, which was constructed using a synthetic fragment from the SpeI site in the chicken signal to the NheI site in the human gene in which the codon at position 4 of the mature protein was changed from GAA (glutamic acid) to GGA (glycine).

DETAILED DESCRIPTION OF THE PREFERRED EMBODIMENTS

Figure 2:
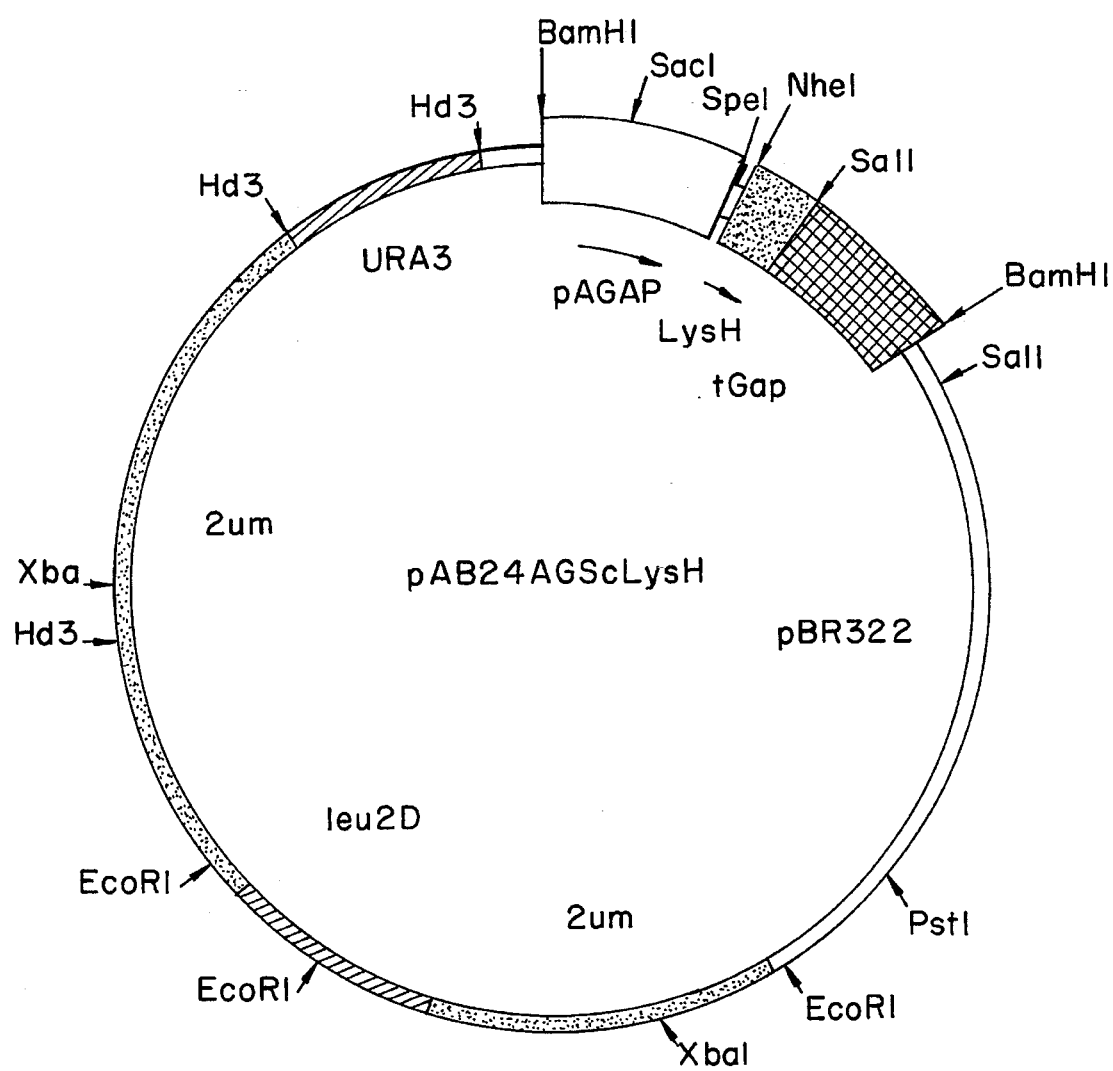
FIG. 2 illustrates plasmid pAB24AGScLysH, which may be used for the expression in yeast of human lysozyme, and which was obtained by insertion into the yeast-E.coli shuttle vector pAB24 of a human lysozyme expression cassette comprising the regulatable ADH2-GAP promoter, chicken lysozyme signal sequence, human lysozyme gene shown in FIG. 1 and GAP terminator.

As emphasized above, the first demonstration of the possibility to make yeast, through genetic engineering techniques, able to produce and to secrete enzymatically-active lysozyme was made with chicken lysozyme as a model compound. More specifically, in example 2.2 of Belgian Patent BE 901,223, there is described the transformation of a leu2 strain of *Saccharomyces cerevisiae* (GRF18) with a plasmid (plys50) comprising the entire sequence of the endogenous 2-micron plasmid, the defective LEU2 gene of plasmid pJDB219 (see J. D. BEGGS, Nature 275, 104, 1978) for selection in yeast, bacterial sequences for replication and selection in *E.coli* and an expression cassette wherein a complete chicken lysozyme cDNA is under the transcription control of the yeast promoter p415. In this example, lysozyme expression and secretion were evidenced by the ability of both a cell homogenate and the cell-free culture medium itself to lyse cells of *Micrococcus lysodeikticus*. Total activity amounted to 162 units/ml, that is 118 units in the medium and 44 units associated with the cells.

The same type of results is obtained when using another 2-micron-based expression plasmid wherein transcription of the chicken lysozyme cDNA is ensured by the strong constitutive promoter of the GAP gene coding for glyceraldehyde phosphate dehydrogenase. In a first attempt to express human lysozyme, we have in this latter construction replaced the DNA portion coding for mature chicken lysozyme by a synthetic DNA segment coding for mature human lysozyme. The sequence used, shown in FIG. 1, was derived primarily in order to utilize codons preferred by *S.cerevisiae* for the high level expression of its own genes. In addition, silent mutations were used to introduce unique restriction enzyme sites for possible subsequent manipulation of the sequence. Unexpectedly, using this construction, no leu$^+$ transformants could even be obtained upon transformation by conventional methods and selection on leucine-deficient medium. Thus, apparently, human lysozyme when actively synthesized in yeast protoplasts reduces cell viability, possibly by interfering with the synthesis of chitin which is a normal constituent of the yeast cell wall (see E. CABIB & R. ROBERTS, Ann. Rev. Biochem. 51, 763, 1982).

However, we have found that when transcription of the same human lysozyme-coding DNA segment is put under the control of a regulatable promoter and provided that derepression thereof is carried out under growth-limited conditions, active lysozyme synthesis takes place without apparent detrimental effect on cell physiology. By contrast, when lysozyme synthesis occurs under conditions permitting growth, not only is biomass production impaired but, still more strikingly, lysozyme synthesis is too limited to be of practical interest. Such a dependence of human lysozyme synthesis on growth-limited conditions is not observed with chicken lysozyme. This is surprising in view of the similarity between the enzymatic properties of both enzymes. At first glance, this difference might be ascribed to the fact that human lysozyme has a specific activity about 2.5 times higher than that of chicken lysozyme (see R. E. CANFIELD et al. in "Lysozyme", Ed. E. F. OSSERMAN, R. E. CANFIELD and S. BEYCHOK, Academic Press, 1974, p. 63). However, when the primary structure of the former is altered by site-directed mutagenesis so that the Glu residue in position 4 is substituted by a Gly residue as in chicken lysozyme, the same inhibition of lysozyme synthesis under growth conditions is observed, whereas the specific activity of the mutated protein with *M.lysodeikticus* as substrate is not significantly higher than that of chicken lysozyme.

Accordingly, it is an important aspect of the present invention to provide a process wherein growth and lysozyme synthesis are substantially consecutive instead of simultaneous events. This can easily be achieved by using for the transcription of the lysozyme-encoding DNA segment a repressible yeast promoter. Various promoters of this type are known. For instance, the promoter of the gene coding for acid phosphatase can be used as taught in European patent EP 100,561. As disclosed recently in European patent EP 213,593, this property is related to the presence, upstream of the PHO5 gene, of two activation sequences which can be used to construct regulatable hybrid promoters, e.g. by fusion with the promoter of the GAP gene. Actually, as described in European patent EP 164,556, a variety of such hybrid promoters can be constructed by combining different yeast promoters, especially strong promoters from genes coding for glycolytic enzymes as GAP, with a regulatory region corresponding to different repressible genes, e.g. GAL1, GAL10, PHO5, SUC2, MAL6S, MAL6T, CYC1, ADH2 or genes under general amino acid control such as HIS1, HIS3, HIS4, TRP5 or LEU3. For instance, the ADH2 gene is repressed by glucose and derepressed in the presence of a non-fermentable carbon source such as ethanol. Thus, by using such regulatable promoters, it is possible, by carefully controlling the composition of the culture medium, to have lysozyme expression switched on or off, independently of growth. Other yeast promoters regulated by a change of temperature can also be used.

As also emphasized above, another important aspect of the present invention is that lysozyme expressed in yeast under growth-limited conditions is secreted therefrom. This is also a surprising fact when it is taken into consideration that most experimental evidences presently available point to the fact that, in yeast, protein secretion is correlated to cell growth (see R. SCHEKMAN, TIBS, July 1982, p. 243). In contrast to this, as the yeast cells are maintained at the stationary phase, the amount of secreted lysozyme found outside the plasma membrane increases at the expense of the amount found intracellularly.

Nevertheless, as those skilled in the art know, in order to ensure secretion of lysozyme through the plasma membrane, it is necessary that the lysozyme-encoding DNA segment be appropriately equipped with a leader sequence coding for a signal peptide allowing the translated protein to be translocated into the lumen of the endoplasmic reticulum and processed into the mature enzyme. This leader sequence can be any sequence coding for any signal peptide, homologous or heterologous, which is recognized and correctly cleaved by the yeast secretion machinery. As already discussed above, efficient secretion results from the use of the sequence encoding the signal peptide of chicken lysozyme but sequences coding for other heterologous signal peptides can also be used. On the other hand, homologous signal sequences can be used. For example, an efficient and well documented secretory expression method consists in using the leader region of the precursors of the yeast mating pherormones alpha- and a-factors (see, e.g., European patents EP 116,201 and EP 123,289).

The lysozyme-encoding DNA segment to be expressed by the process of the invention can be any DNA sequence coding for human lysozyme, i.e. for a protein having muramidase activity and substantially the same amino acid sequence as native human lysozyme. It can be a cDNA obtained by reverse transcription of mRNA transcribed from the native human gene. Alternatively, it can be any synthetic DNA segment encoding human lysozyme as hereabove defined. A significant advantage of the latter method is that the nucleotide sequence of the DNA segment thus synthesized can be so designed as to comprise the codons most frequently used in yeast, in order to improve translation efficiency. In accordance with the above definition, any DNA segment coding for a protein wherein some modifications with respect to native human lysozyme would have been brought for practical purposes, e.g. improved thermal stability and/or specific activity, has to be considered as comprised within the scope of the present invention.

To have lysozyme expressed in yeast and secreted therefrom, an expression cassette comprising those different elements, i.e., from 5' to 3', the repressible promoter, the DNA sequence coding for an appropriate signal peptide, the lysozyme-encoding DNA segment and, preferably, a yeast transcription terminator, has to be constructed and inserted appropriately into a yeast expression vector. One possibility is to make use of a plasmid able to replicate autonomously in yeast in a large number of copies as those where use is made as marker of the defective LEU2 gene. Preferred versions of such expression plasmids are those derived from the yeast endogenous 2-micron plasmid and, still preferably, those comprising the complete sequence thereof. In this case, it is possible to use for transformation cir$^o$ strains of yeast, i.e. strains cured from their 2-micron plasmids. Transformants thus obtained only contain the chimaeric plasmid constructed with the lysozyme gene. The number of copies thereof is therefore maximized and plasmid instability resulting from recombination reactions is minimized. Nevertheless, for maxiumum expression stability, it may be preferred to integrate the expression cassette into the yeast genome. A great number of expression systems can thus be devised by a judicious combination of various construction elements, a large number of which are already available in the art.

The yeast that can be used in accordance with the present invention will preferably be of the genus Saccharomyces and more preferably of the species *Saccharomyces cerevisiae*, i.e. baker's yeast. One reason for this is that the biological properties thereof are relatively well known. Another important reason is that *S.cerevisiae* is typically a GRAS (generally recognized as safe) microorganism, especially suitable for "Good Industrial Large Scale Practice" as defined recently by the Organization for Economic Cooperation and Development (OECD). However, the process of the present invention can also be applied with advantage to other species of yeasts, e.g. *Kluyveromyces lactis, Pichia pastoris, Saccharomycopsis lipolytica, Schwannomyces alluvius, Schizosaccharomyces pombe*, and the like.

As realized by those skilled in the art, when a DNA segment coding for human lysozyme is put under the control of a repressible promoter as described above, it is possible to grow the host organism while avoiding the enzyme to be synthesized. For that, growth conditions such that the promoter remains repressed have to be maintained. For instance, when use is made of the PHO5 promoter, the inorganic phosphate in the culture medium has to be monitored at a sufficiently high value, e.g. by controlled addition of inorganic phosphate to the medium, until the desired cell concentration is obtained. Then, upon interrupting addition and provided that the other nutrients are not in limiting amount, the concentration of inorganic phosphate in the medium will decrease as a result of continued growth so as to reach a value low enough to induce lysozyme synthesis but not to ensure active growth.

Similarly, when use is made of a promoter repressed by glucose and derepressed by ethanol such as the ADH2 promoter, the concentration of glucose should be maintained at a level high enough to ensure growth but not lysozyme synthesis. Such conditions result in the production of ethanol, as a consequence of the so-called Crabtree effect (see for example O. KäPPELI et al., CRC Critical Reviews in Biotechnology 4 (3), 299, 1986). Then, upon interrupting glucose feeding, lysozyme synthesis will take place at the expense of the ethanol thus produced.

According to a preferred way to practice the invention, yeast cultivation and lysozyme production are carried out as separate operations. In a first medium, yeast growth takes place in the absence of lysozyme synthesis up to the desired cell density. Then cells are transferred into a medium selected for ensuring lysozyme synthesis but only limited growth. The major advantage of this method is that optimal conditions for both operations can be applied independently. These operations can be carried out batchwise, semi-continuously as in fed-batch operations, or fully continuously.

Figure 9:
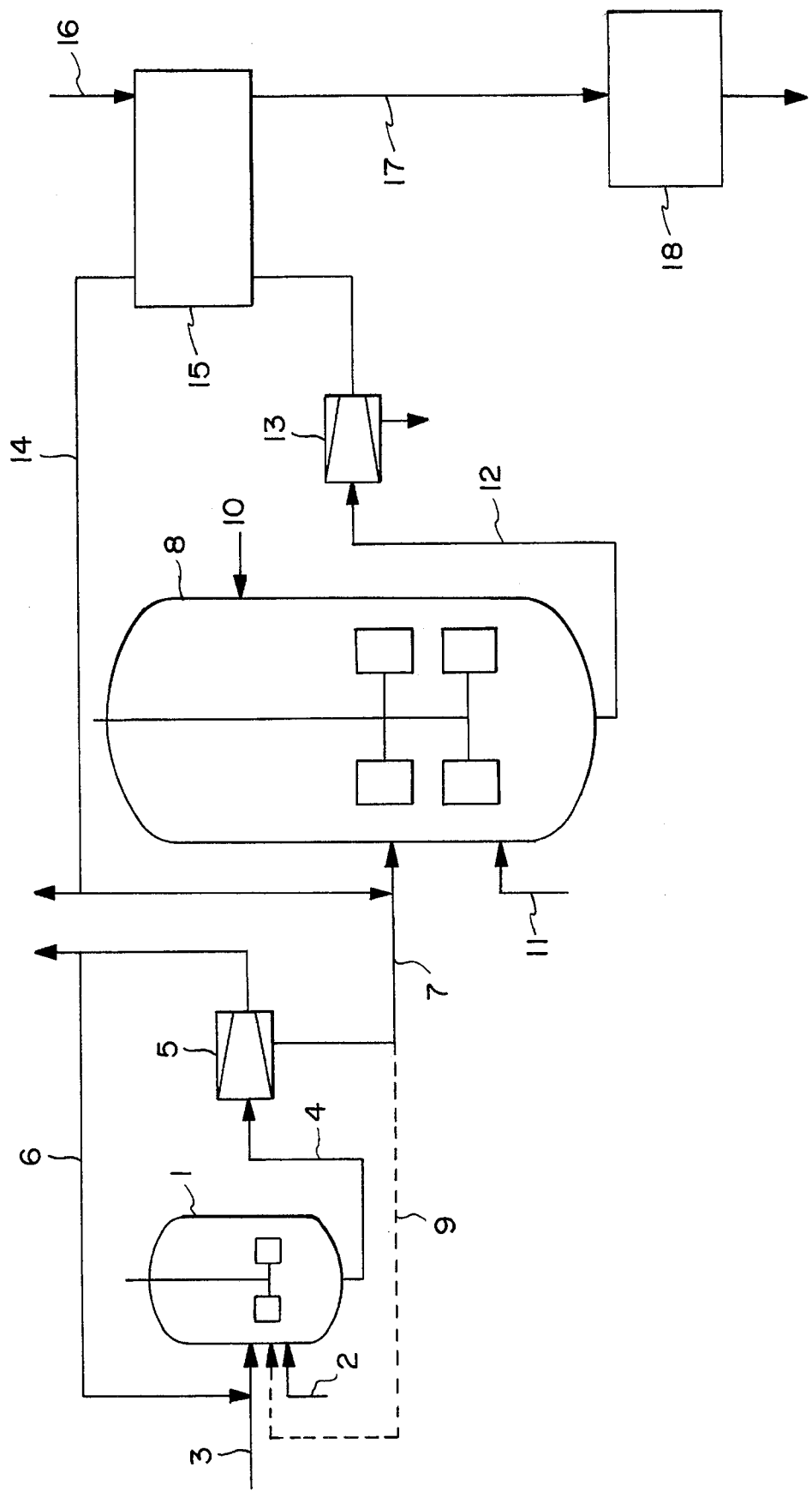
FIG. 9 illustrates a flow sheet of an embodiment of one particular mode of practicing the invention, wherein the secreted lysozyme is recovered by extraction from the liquid medium.

To provide yet more detailed description of the process of the present invention, reference will now be made to FIG. 9, which illustrates a particular mode of practising the invention and therefore should not be considered as limiting its scope. In the process thus illustrated, yeast cultivation is carried out in fermentation tank 1 where provision is made for air from line 2 and of appropriate nutrients from line 3. These nutrients should be supplied in quantities sufficient to ensure active growth but repressed lysozyme synthesis as explained above. They comprise a carbon source which may be pure glucose or sucrose or industrial spent liquors such as molasses. The other nutrients required for growth may be in the form of mineral salts such as $(NH_4)_2SO_4$, and $KH_2PO_4$, which may be supplemented with growth factors such as amino acids, vitamins, and metal salts, as generally used in baker's yeast production. Alternatively, they may be provided in the form of more complex natural products such as yeast extract, peptone, malt extract, and the like.

Yeast cultivation will be conducted up to the highest possible cell concentration compatible with normal process operation. In most cases, the yeast concentration reached in tank 1 will be comprised between 0.5 and 10% of dry weight, preferably between 3 and 6%. Below 0.5%, the volumes to be handled become disproportionate with the amount of useful products to be recovered and above 10% practical problems arise, e.g. from the high viscosity of the cell suspension.

The biomass produced in tank 1 is sent through line 4 to centrifuge 5 where it is concentrated. The clarified medium is at least partly recycled to tank 1 via line 6, the remainder being discarded. The concentrated cell suspension is transferred through line 7 to tank 8. Part of this suspension may also be recycled to tank 1 through line 9; this is especially interesting in continuous operation to achieve high cell density and high productivity of the biomass.

In tank 8, provision is made for nutrients from line 10 and for air from line 11. The conditions therein will be such as to bring complete derepression of the lysozyme expression system, and therefore they depend on the promoter selected to control gene transcription. For the reasons emphasized above, it is also important that these conditions be so adjusted as to limit growth, e.g. by limiting the concentration of some factors required for growth but not for protein synthesis.

The suspension of the lysozyme-producing yeasts is withdrawn from tank 8 through line 12. The cells are separated in centrifuge 13 from the medium which is at least partly recycled to tank 8 via line 14 after treatment for lysozyme extraction in extraction unit 15. This latter operation can easily be achieved by adsorption on ion exchange or affinity materials from which the enzyme can then easily be recovered by elution with, e.g. aqueous NaCl from line 16. The eluate is subsequently sent via line 17 to purification unit 18 where it is subjected to a treatment which may comprise a combination of other classical methods such as ultrafiltration, crystallization, and the like. Finally, a dry product ready for commercialization can be obtained by lymophilization or spray drying (not shown).

Figure 10:
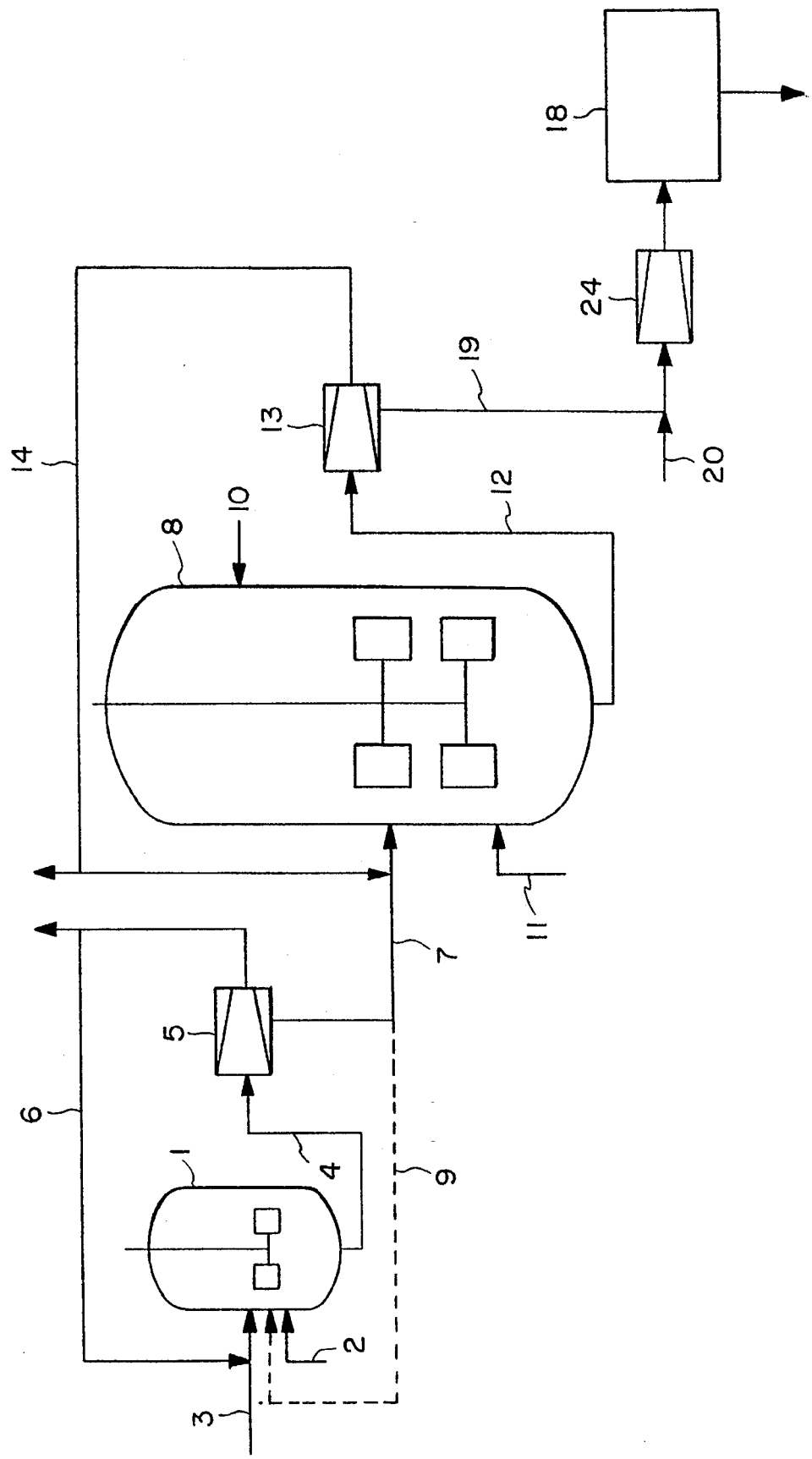
FIG. 10 illustrates a flow sheet of another embodiment of the process wherein lysozyme production is carried out under such conditions that the secreted portion thereof remains associated with the yeast cell wall.

In practising the invention, it may be advantageous, for at least two reasons, to apply in tank 8 conditions such that a major part of the lysozyme secreted from the yeast cells remains associated to the cell wall. The first reason is that cell-associated lysozyme is protected against deactivation which progressively takes place when the enzyme is liberated into the medium. The second reason is that, as taught in Belgian patent BE 903,626, a substantial fraction of said cell-associated lysozyme can be recovered in concentrated form by a simple wash with an aqueous solution of a mineral salt. FIG. 10 shows an embodiment of the process of the invention where such conditions are applied in tank 8. The yeast suspension is withdrawn from tank 8 through line 12. In centrifuge 13, the cells are separated from the medium which is at least partly recycled to tank 8 via line 14, the remainder being discarded. The cells from centrifuge 13 are contacted in line 19 with an aqueous solution of a mineral salt from line 20 whereby the lysozyme associated to the cell wall is liberated therefrom. Said salt should be water-soluble, relatively neutral and preferably nontoxic to the yeast cells. Specific examples are: NaCl, KCl, $NaNO_3$, $KNO_3$, $Na_2SO_4$, $(NH_4)_2SO_4$ and the like. For reasons of economy, NaCl will generally be preferred. The concentration thereof to be used for efficient recovery of the cell-associated lysozyme is not critical and may, for example, be varied between 0.2 and 2.0M. In practice, a concentration of NaCl comprised between 0.5 and 1.0M is used with advantage. Concentrations below 0.5M generally result in a limited recovery with the consequence that a substantial part of the lysozyme produced is lost with the residual cells. On the other hand, concentrations above 1.0M will generally not bring any improvement. The lysozyme thus liberated is then separated from the residual cells in centrifuge 24 and can be further purified in unit 18 by the same techniques as mentioned hereabove. Thus, the yeast cell wall itself can act and can be exploited as an adsorbing material for recovering the enzyme.

To apply this latter mode of operation, it is important to limit the concentration of mineral salts in tank 8. Conversely, if it is preferred to recover the major part of the enzyme from the medium by extraction in unit 15, as in the first-mentioned mode of operation, it is better to increase the concentration of mineral salts in tank 8. For this purpose, the same salts in the same concentration range as defined hereabove for the recovery of cell-associated lysozyme can be used. As the following examples will show, the presence of salt in high concentration may be detrimental for growing yeast but not for yeast producing lysozyme under growth-limited conditions. Therefore, it is a further advantage of the present two-step process to provide means for growing yeast under conditions optimal for biomass production and then inducing lysozyme synthesis under conditions ensuring optimal excretion of the enzyme into the medium.

The residual yeasts obtained from whatever mode of operation can be recovered and used as such eventually after further treatment such as pressing or drying. Such residue can also be partly recycled to tank 8 for further lysozyme production or recycled to fermenter 1 as a source of nutrients and growth factors, eventually after appropriate disrupting treatment.

The above statements as well as other embodiments of the present invention will now be made more apparent by the following examples which are given for illustration only and are not intended to limit the scope of the invention.

EXAMPLES

1. PLASMID-MEDIATED EXPRESSION OF (1) HUMAN LYSOZYME, (2) A GLY-4 MUTANT OF HUMAN LYSOZYME AND (3) CHICKEN LYSOZYME IN YEAST USING THE CHICKEN LYSOZYME SIGNAL SEQUENCE FOR SECRETION 1.1. Construction of the Expression Vectors 1.1.1. Human lysozyme Oligonucleotides corresponding to the sequence of the human lysozyme gene with yeast preferred codons were synthesized using phosphoramidite chemistry on an Applied Biosystems DNA Synthesizer. The individual oligonucleotides were designed using a computer program which maximizes overlaps and minimises incorrect annealing. All of the molecules had a 5' phosphate except for the 5'terminus. The entire gene was annealed and ligated together, and the full length ligation product (see FIG. 1) isolated from an agarose gel. It was then phosphorylated on the 5' terminus with T4 polynucleotide kinase and ligated into plasmid pAGAP1 which had been treated with NcoI and SalI and alkaline phosphatase. pAGAP1 is a derivative of pPGAP (See J. TRAVIS et al., J. Biol. Chem. 260, 4384, 1985) in which the GAP promoter (glyceraldehyde-3-phosphate dehydrogenase gene 491 promoter) has been replaced with the hybrid ADH2-GAP promoter (see L. S. COUSENS et al., Gene 61, 265, 1987). The lysozyme gene was then subjected to dideoxy sequence analysis and the designed sequence was verified. The expression cassette consisting of the ADH2-GAP promoter, chicken lysozyme signal sequence, human lysozyme gene, and GAP terminator was excised with BamH1 and inserted into the yeast—*E.coli* shuttle vector pAB24 (see P. J. BARR et al., J. Exp. Med. 165, 1160, 1987). The resulting plasmid, pAB24AGScLysH, is shown in FIG. 2.

1.1.2. Gly-4 mutant human lysozyme

Figure 4:
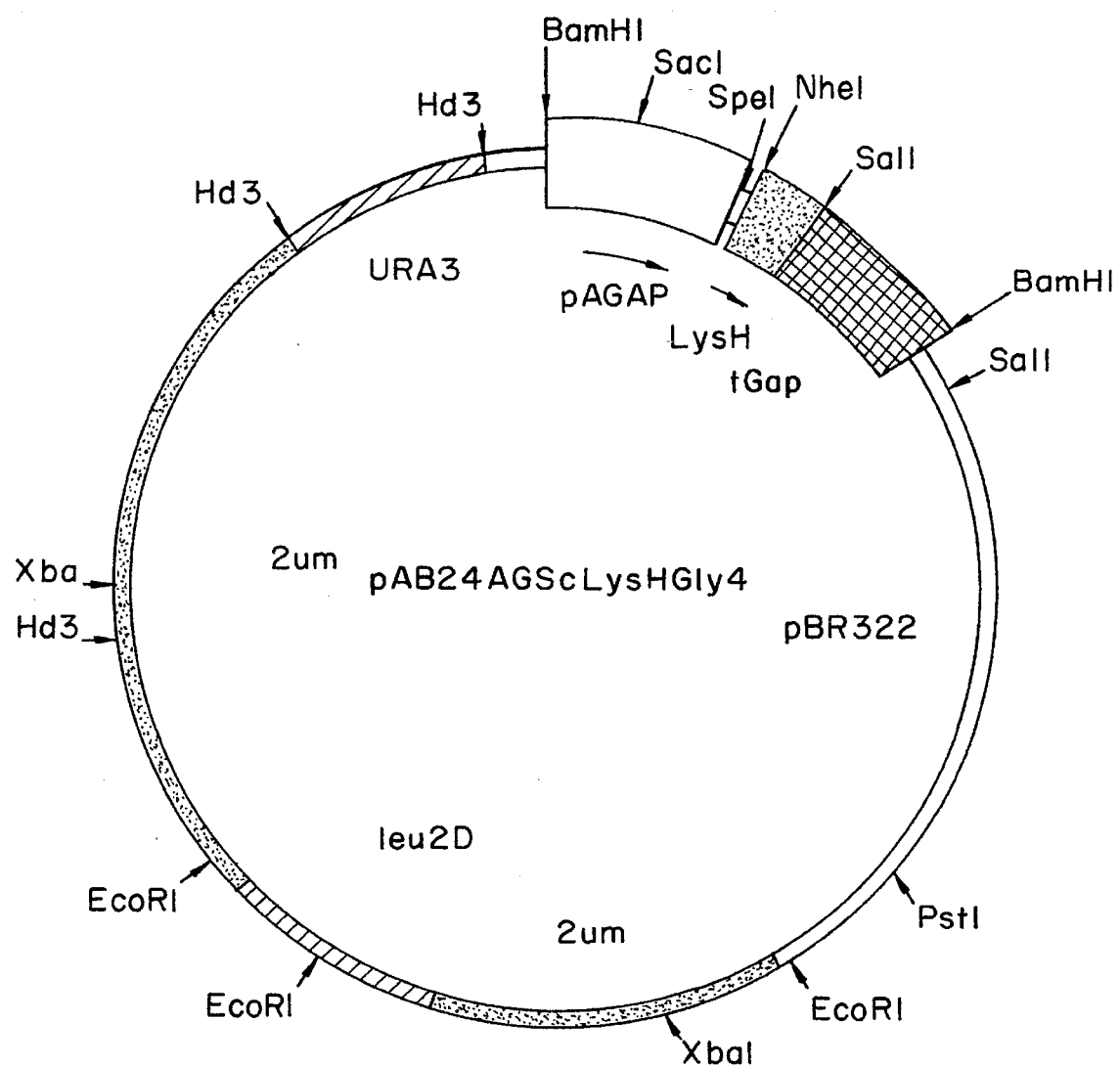
FIG. 4 illustrates plasmid pAB24AGScLysHGly4, which is identical to that shown in FIG. 2 except that the mutant gene of FIG. 3 is substituted for the human lysozyme gene shown in FIG. 1.

In order to make the analogous plasmid containing a mutation in the human lysozyme gene of Glu-4 to glycine (see FIG. 3), standard methods were used to synthesize part of the gene from the SpeI site in the chicken signal to the NheI site in the human gene in which the codon at position 4 of the mature protein was changed from GAA (glutamic acid) to GGA (glycine). Reconstruction of the expression vector yielded the plasmid pAB24AGScLysHGly4, which is shown in FIG. 4.

1.1.3. Chicken lysozyme

Figure 5:
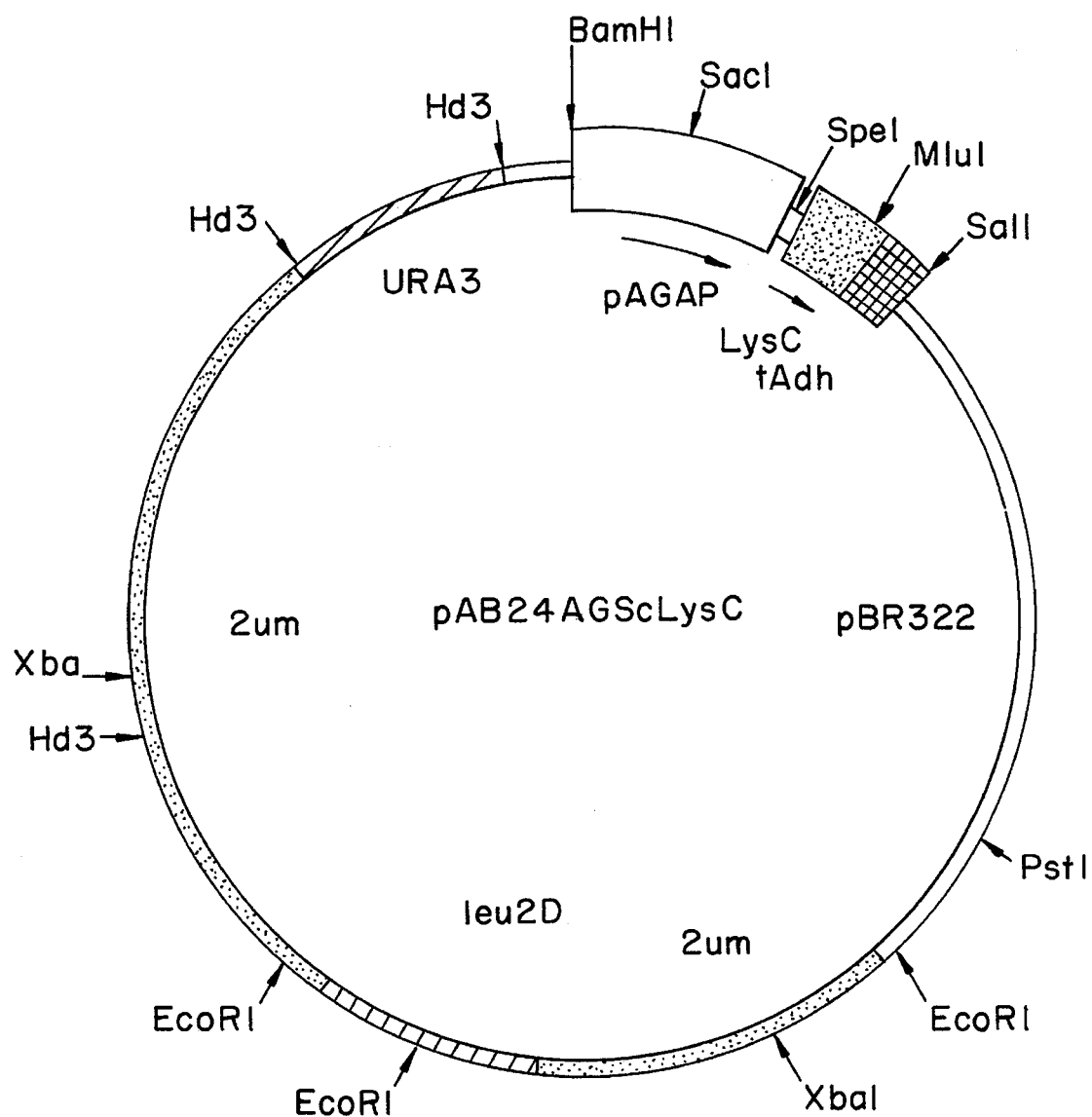
FIG. 5 illustrates plasmid pAB24AGScLysC, which is identical to that shown in FIG. 2 except that the expression cassette consists of the ADH2-GAP promoter, a complete chicken lysozyme cDNA and the ADH1 terminator.

Similar methods could be used to make a plasmid with the chicken lysozyme gene driven by the ADH2-GAP promoter. This plasmid, pAB24AGScLysC, is shown in FIG. 5.

1.2. Expression and secretion of lysozymes in yeast

These three plasmids were transformed into *S.cerevisiae* strain GRF180, a derivative of GRF18 (E. ERHART & C. P. HOLLENBERG, J. Bact. 156, 625, 1983) from which the endogenous 2-micron circle had been cured, and leucine prototrophs selected. Transformants were grown in minimal medium lacking leucine and containing 8% glucose for 2 days at 28° C. They were then used to inoculate cultures of complex medium (YEP:1% yeast extract+2% peptone) containing 8% glucose at a ratio of 1:150 and these cultures were grown at 28° C. at 180 rpm. After 5 days of culture, aliquots of 10 ml were removed, centrifuged at 2500 g for 10 minutes and lysozyme activity determined in the culture supernatant ($S_0$ fraction). Assays were done according to the method of D. SHUGAR (see Biochim. Biophys. Acta 8, 302, 1952) using *Micrococcus lysodeikticus* as substrate. One unit of activity is defined as that amount of enzyme which causes a decrease in absorbance at 450 nm of 0.001 per minute using a suspension of *M.lysodeikticus* in 66 mM potassium phosphate, pH 6.24, at 25° C. in a 1 ml reaction mixture.

Cells from the transformants were suspended in 1 ml of 0.1M sodium phosphate buffer, pH 6.5, containing 0.5M NaCl and incubated for 5 minutes at 4° C. The cells were removed by centrifugation and the lysozyme activity in the salt wash (fraction $S_1$) was determined. In order to determine the amount of lysozyme which was intracellular, the cell pellets were vortexed for 5 minutes with glass beads in 0.1M sodium phosphate buffer, pH 6.5, containing 0.5M NaCl and 0.05% Triton X-100 in a Braun homogenizer. After separation of the cellular debris by centrifugation at 12500 g, lysozyme activity present in the soluble intracellular fraction (fraction $S_2$) was determined.

The results obtained are shown in Table 1.

be released without breaking the cells by the NaCl wash ($S_1$), the latter activity corresponding to that fraction of lysozyme which is secreted but which is still adsorbed to the yeast cell wall.

1.3. Isolation, purification and characterization of the secreted lysozymes

In order to purify the yeast-derived recombinant lysozymes, cultures of the three plasmid transformants in strain GRF180 were grown for 5 days in YEP medium containing 8% glucose as described above. The cells were concentrated by centrifugation for 15 minutes at 2500 g and then they were resuspended in an equal volume of 0.1M sodium phosphate buffer, pH 6.5, containing 0.5M NaCl. After a 60 minute incubation at 4° C., the supernatant was collected by centrifugation, diluted 10 fold with 0.1M sodium phosphate buffer pH 6.5, and loaded on a CM-Sepharose fast flow (Pharmacia) column. After loading was completed, the column was washed with the same buffer and the lysozyme then eluted with the same buffer containing 0.5M NaCl. Fractions containing lysozyme activity determined as described above were pooled, concentrated by ultrafiltration on an Amicon Diaflow membrane, desalted on a Sephadex G-25 column and lyophilized.

The specific activities of the lysozyme preparations were determined by first measuring the lysozyme activity as described above and using the Biorad protein assay with chicken lysozyme as standard to measure protein concentrations. The results are shown in Table 2.

TABLE 2

| Specific activities of purified lysozymes | | |
|---|---|---|
| Lysozyme | Origin | Specific activity (units per microgram of protein) |
| Human | Milk | 756 |
|  | Yeast | 727 |
| Human Gly-4 | Yeast | 281 |
| Chicken | Egg white | 263 |
|  | Yeast | 302 |

Based on the values given therein, the total synthesis of the three lysozymes in glucose medium as shown in table 1 is 17, 19 and 19 mg/l for human, human mutant and chicken lysozyme respectively. SDS polyacrylamide gel analysis showed that all three samples migrated as single bands

TABLE 1

| Expression of various lysozyme genes using the regulated ADH2-GAP promoter | | | | | | | | |
|---|---|---|---|---|---|---|---|---|
|  |  |  | Lysozyme activity (U/ml) | | | | | Plasmid stability |
| Lysozyme | Medium | OD | $S_o$ | $S_1$ | $S_2$ | Total | U/OD | (%) |
| Human | Glucose | 29 | 48 | 2854 | 9660 | 12562 | 433 | 97 |
|  | Ethanol | 16 | 0 | 114 | 82 | 196 | 12 | 11 |
| Human Gly-4 | Glucose | 32 | 0 | 731 | 4616 | 5347 | 167 | 90 |
|  | Ethanol | 17 | 0 | 46 | 12 | 58 | 3 | 39 |
| Chicken | Glucose | 34 | 452 | 1400 | 3930 | 5782 | 170 | 97 |
|  | Ethanol | 18 | 208 | 270 | 1070 | 1548 | 86 | 95 |

Total lysozyme activity was 433 U/OD (units of activity per unit of optical density) for human and 167 and 170 U/OD for human mutant and chicken lysozyme, respectively, when grown in glucose. In all three cases between 14 and 32% of the total activity is secreted: it is found in the medium ($S_0$) and/or associated to the cells from which it can having the same mobilities as the appropriate controls: human milk lysozyme for the human proteins and egg-white lysozyme for the chicken enzyme. When subjected to automated Edman degradation, all three proteins had a single N-terminus of lysine, and further sequence analysis gave the sequences expected from the DNA sequences. Thus, the chicken signal sequence is processed correctly from all three proteins.

Comparative Example 1

The growth protocol described in Example 1.2 was repeated for all three proteins except that 1% ethanol was used as carbon source instead of 8% glucose. This medium is such that cell growth and lysozyme synthesis occur simultaneously. When lysozyme activity in the three cultures was determined, the results shown in Table 1 were obtained. For both the human and human mutant proteins, growth in ethanol decreased lysozyme production dramatically to less than 5% of the levels when cells were grown in 8% glucose. In contrast, chicken lysozyme expression was only decreased to 50% of the level observed in the 8% glucose culture.

These results clearly demonstrate that for achieving in yeast a synthesis of human lysozyme (authentic or mutant, not chicken) active enough to be of practical interest, it is necessary to work under such conditions that, in accordance with the invention, growth does not simultaneously take place.

Further tests were still carried out to estimate plasmid stability under the culturing conditions used in the above Examples. These tests consist in determining on Petri dishes the fraction of yeast cells still displaying leucine prototrophy at the end of the experiment, i.e., cells having retained the lysozyme expression plasmid. The results thus obtained are also quoted in Table 1. They show that in the case of human lysozyme (authentic or mutant, not chicken), cells grown in the presence of ethanol have substantially lost the plasmid. Thus, it appears that growth is so impaired by human lysozyme synthesis that cells having lost the plasmid as a result of mitotic segregation rapidly overcome those still bearing the plasmid.

Comparative Example 2

Figure 6:
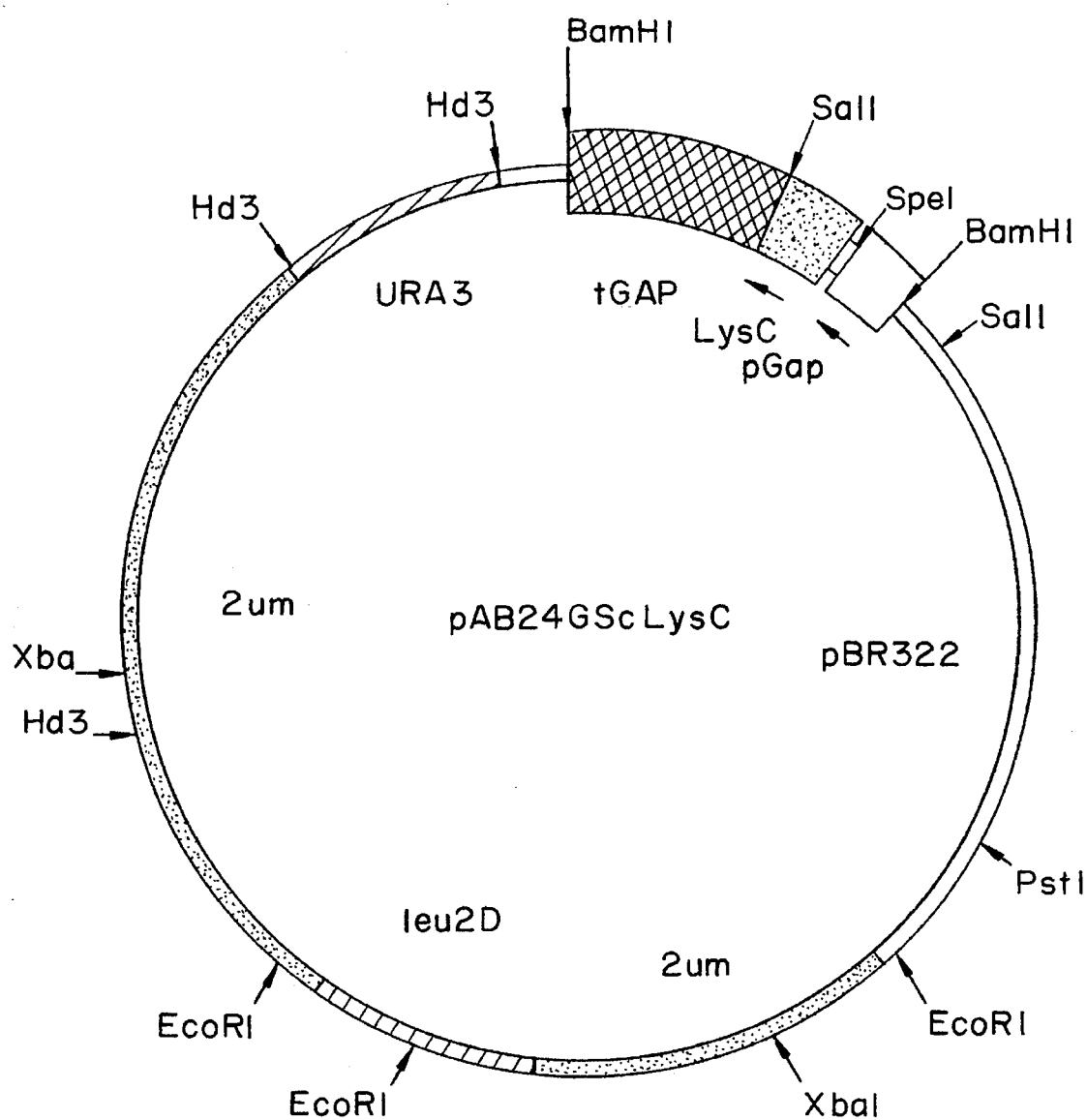
FIG. 6 illustrates plasmid pAB24GScLysC, which is identical to that shown in FIG. 2 except that the expression cassette consists of the constitutive GAP promoter, the same chicken lysozyme cDNA as shown in FIG. 5 and the GAP terminator.

Using standard methods, the three lysozyme genes whose expression in yeast is illustrated in Example 1 were inserted into expression cassettes using the strong constitutive GAP promoter. The chicken lysozyme construct is shown in FIG. 6; the human and human mutant plasmids are identical except for the lysozyme genes. When these plasmids were transformed into strain GRF180 and leucine prototrophs selected, no transformants could be obtained with the human and human mutant plasmids, whereas transformants were easily obtained with the chicken lysozyme expression plasmid. These transformants were grown as described in Example 1 and lysozyme activity determined. Total chicken lysozyme activity was 110 U/OD as compared to 173 U/OD for the regulated expression plasmid bearing the ADH2-GAP promoter.

This confirms the conclusion drawn from Comparative Example 1 that the synthesis of human lysozyme is detrimental for growing yeast cells. To ascertain that this effect is not restricted to the specific yeast strain used in the above experiments, the transformation protocol of this comparative example was repeated with strain AH22 (A. HINNEN et al., Proc. Natl. Acad. Sci. USA 75, 1929, 1978), strain S150-2B (C. HADFIELD et al., Gene 52, 59, 1987), strain Y-294 (G. S. BRUGGE et al., Mol. Cell. Biol. 7, 2180, 1987) and strain MC16 cir$^o$ (A. B. FUTCHER & B. S. COX, J. Bact. 157, 283, 1984). Substantially the same results were obtained as with strain GRF180.

2. PLASMID-MEDIATED EXPRESSION OF HUMAN LYSOZYME IN YEAST USING THE ALPHA FACTOR LEADER FOR SECRETION

2.1 Construction of the Expression Vector

Figure 7:
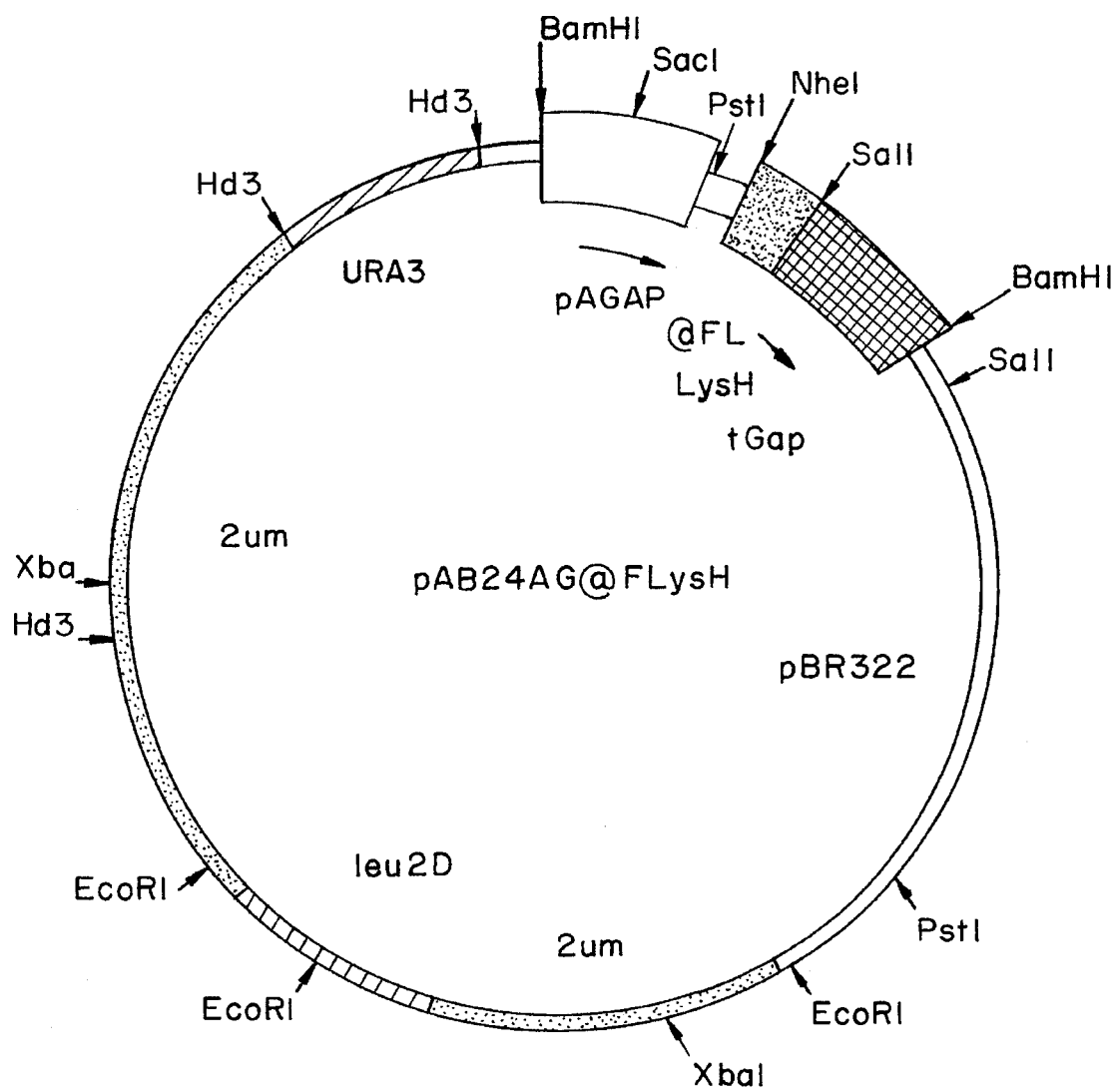
FIG. 7 shows plasmid pAB24AGalphaFLysH, which is substantially identical to that shown in FIG. 2 except that the alpha factor leader sequence is substituted for the chicken lysozyme signal sequence.

Plasmid pAB24AGalphaFLysH (see FIG. 7) was made by isolating the NheI-BamH1 fragment containing most of the human lysozyme gene without the chicken signal sequence and the GAP terminator from plasmid pAB24AGScLysH (FIG. 2). A synthetic Xba-Nhe adapter was used to link this fragment to a BamH1-Xba fragment containing the ADH2-GAP promoter fused to the alpha factor leader (see A. J. BRAKE et al., Proc. Natl. Acad. Sci. USA 81, 4642, 1984). The resulting BamH1 expression cassette consisting of promoter; alpha factor leader, human lysozyme gene, and terminator was inserted into plasmid pAB24, yielding pAB24AGalphaFLysH shown in FIG. 7.

2.2 Expression and secretion of human lysozyme

This plasmid was transformed into yeast strain GRF180, a cir$^o$ derivative of GRF18, and leucine prototrophs selected. Transformants were groom in leucine selective medium containing 8% glucose for 2 days and then diluted 1:20 into YEP medium containing 2% glucose. After 3 days of growth at 30° C., cells were harvested and lysozyme activity determined as described above. The results are shown in Table 3.

TABLE 3

Expression and secretion of human lysozyme using the alpha factor leader

| Plasmid | Medium | Lysozyme activity (U/ml) | | |
|---|---|---|---|---|
| | | $S_o + S_1$ | $S_2$ | Total |
| pAB24 | YEP + 2% glucose | 0 | 0 | 0 |
| PAB24AGalphaFLysH | YEP + 2% glucose | 114 | 136 | 250 |

Clearly, lysozome is expressed and secreted by the alpha factor leader lysozyome fusion constructs, although the levels are lower than with the chicken signal.

3. INTEGRATION-MEDIATED EXPRESSION OF HUMAN LYSOZYME IN YEAST

3.1 Construction of the Integration Vector

Figure 8:
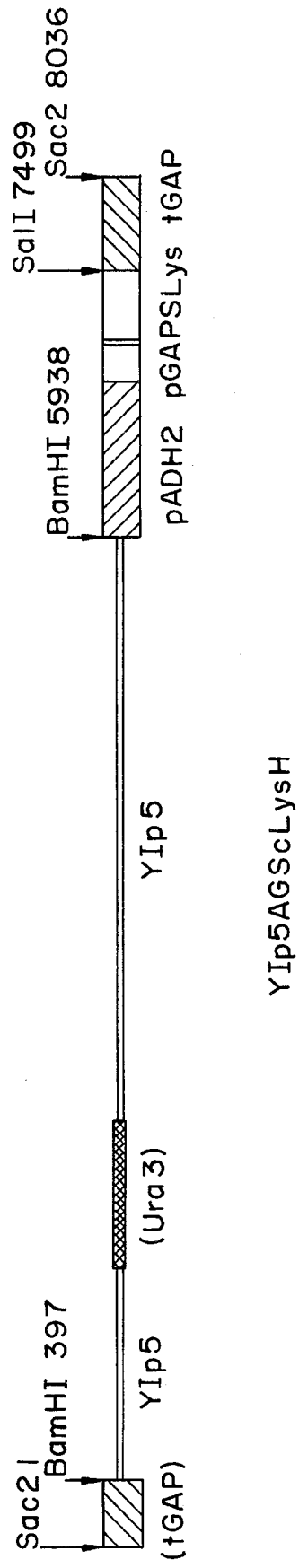
FIG. 8 shows plasmid YIP5AGScLysH, which was obtained by insertion into integration plasmid YIP5 of the same human lysozyme expression cassette as used for the construction of plasmid pAB24AGScLysH shown in FIG. 2.

The human lysozyme expression cassette whose construction is described in Example 1.1 was excised out of plasmid pAB24AGScLysH (see FIG. 2) by digestion with restriction enzyme BamH1 and inserted into integration plasmid YIP5 (see K. STRUHL et al , Proc. Natl. Acad. Sci USA 76, 1035, 1979) yielding plasmid YIP5AGScLysH shown in FIG. 8.

3.2 Expression and secretion of human lysozyme

This plasmid was linearized with Sac2 in the GAP terminator and then transformed into strain GRF181, an ura3 deletion derivative of GRF180. Uracil prototrophs were selected on uracil selective plates containing 8% glucose. Transformants were then grown in uracil-selective medium containing 8% glucose and diluted 1:20 into YEP medium containing 8% glucose for expression. After 5 days, the cultures were harvested and lysozyme activity measured as described above. The results are shown in Table 4. Lysozyme activity was clearly demonstrated for these integrants but levels were lower than those seen for the plasmid-mediated expression under the same conditions.

TABLE 4

Expression of human lysozyme from GRF181 integrants

| | Integrant N° | | | | | |
|---|---|---|---|---|---|---|
| | 1 | 2 | 3 | 4 | 5 | 6 |
| OD | 23 | 23 | 21 | 22 | 21 | 22 |
| Lysozyme activity | | | | | | |
| $S_o + S_1$ (U/ml) | 601 | 282 | 207 | 139 | 174 | 1397 |
| $S_2$ (U/ml) | 224 | 128 | 64 | 73 | 374 | 59 |
| Total | 825 | 410 | 271 | 211 | 548 | 1456 |
| U/OD | 36 | 18 | 13 | 10 | 26 | 66 |

4. INFLUENCE OF SODIUM CHLORIDE ON THE DISTRIBUTION OF HUMAN GLY-4 MUTANT LYSOZYME IN CULTURES OF TRANSFORMED YEASTS

The yeast strain GRF180 transformed with plasmid pAB24AGScLysHGly4 (see FIG. 4) was grown in minimal medium lacking leucine and containing 8% glucose for 3 days at 28° C. The resulting culture was then used to inoculate at 1:150 ratio a complex YEP medium containing 8% glucose. The same protocol for lysozyme determination as described in Example 1 was applied to the cultures obtained after 89 and 209 hours of incubation at 28° C. To determine the effect of mineral salt on lysozyme distribution, an aliquot part of the culture was supplemented with NaCl to 0.5M NaCl after 89 hours and incubation was continued as in the control culture. In another experiment using the same inoculum, 0.5 NaCl was present from the start of the culture.

The results obtained are set forth in Table 5.

TABLE 5

Influence of NaCl on the secretion of human Gly-4 mutant lysozyme from transformed yeasts

| Incubation time (hr) | NaCl (0.5 M) | OD | Lysozyme activity | | Lysozyme distribution (%) | | |
|---|---|---|---|---|---|---|---|
| | | | U/ml | U/OD | $S_o$ | $S_1$ | $S_2$ |
| 89 | – | 33 | 3626 | 110 | 0 | 11 | 89 |
| 209 | – | 33 | 3946 | 120 | 2 | 30 | 68 |
| 209 | + | 27 | 3436 | 127 | 52 | 3 | 45 |
| 89 | + | 21 | 1562 | 74 | 29 | 1 | 70 |
| 209 | + | 22 | 1542 | 70 | 67 | 2 | 31 |

The data in Table 5 show that in conventional YEP medium, most of the lysozyme is found intracellularly ($S_2$ fraction), the more so as the incubation time is lower. By contrast, when NaCl is added to the system, lysozyme is mainly found in the $S_0+S_1$ fraction, i.e. is predominantly secreted. Substantially, the same lysozyme distribution is obtained when NaCl is present from the start of the culture; however, in this case, growth is somewhat inhibited.

The same type of results are obtained with yeasts transformed to produce authentic human lysozyme.

5. INFLUENCE OF A SYNTHETIC YEAST CULTURE MEDIUM ON THE SYNTHESIS AND SECRETION OF HUMAN LYSOZYME

The yeast strain GRF180 transformed with plasmid pAB24AGScLysH (see FIG. 2) was grown in minimal medium lacking leucine and containing 8% glucose for 3 days at 28° C., the resulting culture was then used to inoculate at a 1:6 ratio a complex YEP medium which contained 8% glucose. After 48 hours at 28° C., the cells were harvested by centrifugation and resuspended in the same volume of a synthetic medium whose composition is given in Table 6.

TABLE 6

Synthetic medium for the synthesis and secretion of human lysozyme

| | |
|---|---|
| $KH_2PO_4$ | 6 g |
| $MgSO_4.7H_2O$ | 3 g |
| $CaCl_2.2H_2O$ | 0.1 g |
| NaCl | 0.1 g |
| $(NH_4)_2SO_4$ | 40 g |
| Casein hydrolysate | 20 g |
| Vitamin mix. | 10 ml |
| Biotin | 0.002% |
| Folic acid | 0.002% |
| Calcium panto | 0.4% |
| Nicotinic acid | 0.4% |
| Pyridoxine · HCl | 0.4% |
| Thiamine · HCl | 0.4% |
| p-Aminobenzoic acid | 0.2% |
| Riboflavin | 0.2% |
| Myoinositol | 2.0% |
| Trace elements solution | 10 ml |
| $MnSO_4$ | 0.4% |
| $ZnSO_4$ | 0.4% |
| $FeCl_2$ | 0.2% |
| Sodium molybdate | 0.2% |
| Boric acid | 0.5% |
| Cupric sulfate | 0.04% |
| KI | 0.1% |
| Nucleotides and amino acids supplements | 40 ml |
| Adenine | 1% |
| Uridine | 1% |
| Tryptophane | 1% |
| Methionine | 1% |
| Cysteine | 1% |
| Threonine | 1% |
| Histidine | 0.05% |
| Water | q.s.p. 1 liter |

For the sake of comparison, an aliquot part of the cells was resuspended in a fresh YEP medium. Both media were supplemented with 8% glucose. The resulting suspensions were then further incubated at 28° C. for 90 hours and the lysozyme distribution in the cultures determined as explained in Example 1.

The results obtained are shown in Table 7.

TABLE 7

Influence of the medium on the synthesis and secretion of human lysozyme by transformed yeasts

| Medium (+8% glucose) | | Lysozyme activity | | Lysozyme distribution (%) | | |
|---|---|---|---|---|---|---|
| | OD | U/ml | U/OD | $S_o$ | $S_1$ | $S_2$ |
| Synthetic | 59 | 10992 | 186 | 68 | 5 | 27 |
| Complex (YEP) | 56 | 6542 | 117 | 4 | 19 | 77 |

The data in Table 7 confirm those of the preceding example in that YEP medium, although favorable for growth, does not promote extensive secretion: about ¾ of the lysozyme produced remains intracellular. By contrast, in the synthetic medium used, about ¾ of the lysozyme is secreted, 93% of which being released into solution, i.e., in a form easily recoverable by conventional means, e.g. ultrafiltration.

However, other experiments have shown that this synthetic medium does not ensure especially active growth. Thus, again, it appears that it is important, in accordance with the present invention, to dissociate biomass production from lysozyme synthesis and select separately the conditions of both steps in order to achieve optimum production of human lysozyme.

What is claimed is:

1. A process for producing human lysozyme from Saccharomyces yeast cells whose DNA has been genetically engineered to include a segment coding for human lysozyme, wherein the human lysozyme impairs the growth of the yeast cells, said process comprising the steps of:

contacting growing Saccharomyces yeast cells whose DNA has been genetically engineered to include a segment coding for human lysozyme, wherein the human lysozyme impairs the growth of the yeast cells, with a culture medium, growing the contacted yeast cells up to the stationary yeast cell phase, and then inducing said yeast cells to synthesize and secrete human lysozyme.

2. The process of claim 1, wherein the induction of lysozyme synthesis is caused by a regulatable promoter.

3. The process of claim 1, wherein at least 50% of the lysozyme is secreted into the culture medium.

4. The process of claim 1, wherein at least 50 percent of the lysozyme secreted remains associated with the yeast cell wall.

5. The process of claim 1, wherein the lysozyme produced and secreted by the yeast cells is a mutant of human lysozyme wherein the codon at position 4 is glycine.

6. The process of claim 2, wherein said promoter is a repressible promoter and wherein lysozyme synthesis is induced by derepressing the promoter.

7. The process of claim 2, wherein said promoter is selected from the group consisting of PHO5, ADH2, GAL1, GAL10, SUC2, MAL6S, MAL6T, CYC1, promoters of genes under general amino acid control, thermosensitive promoters, hybrid promoters constructed therefrom and the ADH2-GAP hybrid promoter.

8. The process of claim 7, wherein the promoter is the ADH2-GAP hybrid promoter.

9. The process of claim 7, wherein said promoter is selected from the group consisting of PHO5 and a hybrid promoter constructed with an upstream activation sequence of PHO5.

10. The process of claim 3, wherein said culture medium contains an amount of a mineral salt effective to liberate lysozyme from the wall of said yeast cells into said culture medium.

11. The process of claim 10, wherein the concentration of said mineral salt is less than 0.2M.

12. The process of claim 10, wherein said mineral salt is water-soluble and nontoxic to said yeast cells.

13. The process of claim 10, wherein said mineral salt is selected from the group consisting of NaCl, KCl, NaNO$_3$, Na$_2$SO$_4$ and (NH$_4$)$_2$SO$_4$.

14. The process of claim 10, wherein the concentration of said mineral salt is from 0.2 to 2M.

15. The process of claim 13, wherein said mineral salt is NaCl.

16. The process of claim 14, wherein the concentration of said mineral salt is from 0.5 to 1M.

17. A process for producing human lysozyme from Saccharomyces yeast cells whose DNA has been genetically engineered to include a segment coding for human lysozyme, wherein the human lysozyme impairs the growth of the yeast cells, said process comprising the steps of:

growing Saccharomyces yeast cells whose DNA has been genetically engineered to include a segment coding for human lysozyme, wherein the human lysozyme impairs the growth of the yeast cells, in a culture medium that represses synthesis of human lysozyme, contacting said growing yeast cells with a culture medium and continuing growing the yeast cells up to the stationary yeast cell phase, and then inducing said yeast cells to synthesize and secrete human lysozyme.

18. The process of claim 17, wherein the induction of lysozyme synthesis is caused by a regulatable promoter.

19. The process of claim 17, wherein at least 50% of the lysozyme is secreted into the culture medium.

20. The process of claim 17, wherein at least 50% of the lysozyme secreted remains associated with the yeast cell wall.

21. The process of claim 17, wherein the lysozyme produced and secreted by the yeast cells is a mutant of human lysozyme wherein the codon at position 4 is glycine.

22. The process of claim 18, wherein said promoter is a repressible promoter and wherein lysozyme synthesis is induced by derepressing the promoter.

23. The process of claim 18, wherein said promoter is selected from the group consisting of PHO5, ADH2, GAL1, GAL10, SUC2, MAL6S, MAL6T, CYC1, promoters of genes under general amino acid control, thermosensitive promoters, hybrid promoters constructed therefrom and the ADH2-GAP hybrid promoter.

24. The process of claim 23, wherein the promoter is the ADH2-GAP hybrid promoter.

25. The process of claim 23, wherein said promoter is selected from the group consisting of PHO5 and a hybrid promoter constructed with an upstream activation sequence of PHO5.

26. The process of claim 19, wherein said culture medium contains an amount of a mineral salt effective to liberate lysozyme from the wall of said yeast cells into said culture medium.

27. The process of claim 26, wherein said mineral salt is water-soluble and nontoxic to said yeast cells.

28. The process of claim 26, wherein the concentration of said mineral salt is less than 0.2M.

29. The process of claim 26, wherein said mineral salt is selected from the group consisting of NaCl, KCl, NaNO$_3$, Na$_2$SO$_4$ and (NH$_4$)$_2$SO$_4$.

30. The process of claim 26, wherein the concentration of said mineral salt is from 0.2 to 2M.

31. The process of claim 29, wherein said mineral salt is NaCl.

32. The process of claim 30, wherein the concentration of said mineral salt is front 0.5 to 1M.

33. A synthetic gene for human lysozyme comprising the following sequence

```
AAGGTTTTCGAAAGATGTGAGCTAGCTAGAACTTTGAAGAGATTGGGTATGGACGGTTACAGAGGTATCTCCTTGGCTAACTGGAT
TTCCAAAAGCTTTCTACACTCGATCGATCTTGAAACTTCTCTAACCCATACCTGCCAATGTCTCCATAGAGGAACCGATTGACCTA

GTGTTTGGCCAAGTGGGAATCTGGTTACAACACCAGAGCTACCAACTACAACGCTGGTGACAGATCTACCGACTACGGTATCTTCCA
CACAAACCGGTTCACCCTTAGACCAATGTTGTGGTCTCGATGGTTGATGTTGCGACCACTGTCTAGATGGCTGATGCCATAGAAGGT

AATCAACTCCAGATACTGGTGTAACGACGGTAAGACCCCAGGTGCTGTTAACGCTTGTCACTTGTCCTGTTCTGCTTTGTTGCAAG
TTAGTTGAGGTCTATGACCACATTGCTGCCATTCTGGGGTCCACGACAATTGCGAACAGTGAACAGGACAAGACGAAACAACGTTC

ACAACATCGCTGACGCTGTCGCCTGTGCTAAGAGAGTTGTTAGAGACCCACAAGGTATCAGAGCTTGGGTTGCTTGGAGAAACAGA
TGTTGTAGCGACTGCGACAGCGGACACGATTCTCTCAACAATCTCTGGGTGTTCCATAGTCTCGAACCCAACGAACCTCTTTGTCT

TGTCAAAACAGAGACGTTAGACAATACGTCCAAGGTTGTGGTGTT
ACAGTTTTGTCTCTGCAATCTGTTATGCAGGTTCCAACACCACAA
```

34. A Saccharomyces yeast cell genetically engineered to express the synthetic gene of claim 33, the 5' end of the synthetic gene being fused in phase with a leader sequence coding for a signal peptide that is recognized and correctly cleaved by the yeast secretion machinery.

35. The yeast cell of claim 34, wherein the leader sequence encodes the signal peptide of chicken lysozyme.

36. The yeast cell of claim 34, wherein the expression of the synthetic gene is controlled by a regulatable promoter.

37. The yeast cell of claim 34, wherein the cell is *Saccharomyces cerevisiae*.

38. The yeast cell of claim 34, wherein the synthetic gene is a synthetic gene for a mutant of human lysozyme wherein the codon at position 4 is glycine.

39. The yeast cell of claim 36, wherein said promoter is a repressible promoter, and wherein lysozyme production may be induced by derepressing the promoter.

40. The yeast cell of claim 36, wherein the promoter is selected from the group consisting of PHO5, ADH2, GAL1, GAL10, SUC2, MAL6S, MAL6T, CYC1, promoters of genes under general amino acid control, thermosensitive promoters, hybrid promoters constructed therefrom and the ADH2-GAP hybrid promoter.

41. The yeast cell of claim 40, wherein the promoter is the ADH2-GAP hybrid promoter.

42. The yeast cell of claim 40, wherein said promoter is selected from the group consisting of PHO5 and a hybrid promoter constructed with an upstream activation sequence of PHO5.

43. The yeast cell of claim 37, wherein the cell is selected from the group consisting of strains GRF18, GRF180, AH22, MC16 cir°, S150-2B and Y-294.

* * * * *